United States Patent [19]

Doria et al.

[11] 4,160,028

[45] Jul. 3, 1979

[54] SUBSTITUTED 2-CYCLOPROPYL-CHROMONES AND PHARMACEUTICAL COMPOSITIONS AND USE THEREOF

[75] Inventors: Gianfederico Doria, Milan; Ciriaco Romeo, Serino; Maria L. Corno; Francesco Lauria, both of Milan; Piero Sberze, Varese; Marcellino Tibolla, Canale d'Agordo, all of Italy

[73] Assignee: Carlo Erba S.p.A., Milan, Italy

[21] Appl. No.: 921,853

[22] Filed: Jul. 3, 1978

[30] Foreign Application Priority Data

| Aug. 2, 1977 [IT] | Italy | 26399 A/77 |
|---|---|---|
| Jun. 22, 1978 [IT] | Italy | 24824 A/78 |
| Jun. 22, 1978 [IT] | Italy | 24825 A/78 |
| Jun. 30, 1978 [IT] | Italy | 25157 A/78 |

[51] Int. Cl.$^2$ .............. A61K 31/35; A61K 31/38; A61K 31/44; C07D 311/22

[52] U.S. Cl. .......... 424/248.51; 260/326.34; 260/332.2 A; 260/345.2; 424/248.55; 424/263; 424/267; 424/274; 424/275; 424/283; 544/131; 544/146; 544/151; 546/194; 546/196; 546/269

[58] Field of Search ............. 260/326.34, 332.2 A, 260/345.2; 544/131, 146, 151; 546/194, 196, 269; 424/248.51, 248.55, 263, 267, 274, 275, 283

[56] References Cited

U.S. PATENT DOCUMENTS 4,018,798   4/1977   Cohen et al. .............. 260/345.2

FOREIGN PATENT DOCUMENTS 844884   8/1975   Belgium.
844943   8/1975   Belgium.

*Primary Examiner*—Richard Raymond
*Attorney, Agent, or Firm*—Murray and Whisenhunt

[57] ABSTRACT

Substituted 2-cyclopropylchromones, process of preparation, pharmaceutical compositions and method of treating allergies are disclosed.

12 Claims, No Drawings

SUBSTITUTED 2-CYCLOPROPYL-CHROMONES AND PHARMACEUTICAL COMPOSITIONS AND USE THEREOF

The present invention relates to substituted 2-cyclopropylchromones, to a process for their preparation and to pharmaceutical compositions containing them.

The compounds of the invention have the following formula (I)

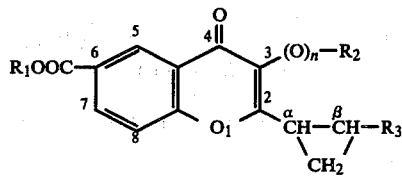

wherein
n is zero or 1;
$R_1$ is hydrogen or $C_1$–$C_{20}$ alkyl, unsubstituted or substituted by a $C_2$–$C_5$ alkanoyloxy or by a

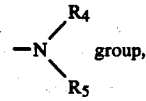

wherein each of $R_4$ and $R_5$ is independently selected from the group consisting of hydrogen and $C_1$–$C_{10}$ alkyl, or $R_4$ and $R_5$, taken together with the nitrogen atom, form a N-pyrrolidinyl, piperidino or morpholino radical;
$R_2$ is $C_1$–$C_8$ alkyl or $C_3$–$C_4$ alkenyl;
$R_3$ is (a) furyl, thienyl or pyridyl, the furyl, thienyl and pyridyl groups being unsubstituted or substituted by a methyl group; or (b) the group

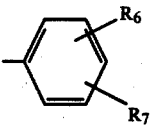

wherein each of $R_6$ and $R_7$ is independently selected from the group consisting of (a') hydrogen; (b') halogen; and (c') the group —$(O)_{n_1}$—$R_8$, wherein $n_1$ is zero or 1 and $R_8$ is $C_3$–$C_4$ alkenyl or $C_1$–$C_6$ alkyl, the alkenyl and the alkyl groups being unsubstituted or substituted by one or more $C_1$–$C_2$ alkoxy or hydroxy groups.

Object of the present invention are also the pharmaceutically acceptable salts of the compounds of formula (I), as well as all the possible isomers and the mixtures thereof.

The compounds of the invention may be either in the cis- or in the trans-configuration. When the two hydrogen atoms on the α and on the β carbon atoms are on the same side in respect of the plane of the cyclopropane ring, the compounds are in the cis-configuration and vice versa. Also the mixture of the cis- and trans-isomers is included in the scope of the present invention.

Preferably the compounds of the invention are in the trans-configuration.

The numbering used to identify the position of the substituents in the $R_3$ radical is the conventional one, as is shown by the following examples:

(a) when $R_3$ is phenyl:

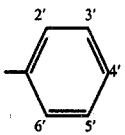

(b) when $R_3$ is pyridyl:

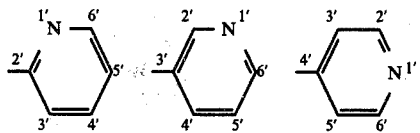

(c) when $R_3$ is furyl or thienyl:

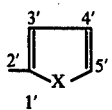

wherein X is oxygen or sulphur.

The alkyl, alkenyl, alkoxy and alkanoyloxy groups may be branched or straight chain groups.

When $R_1$ is an unsubstituted $C_1$–$C_{20}$ alkyl, it is preferably $C_1$–$C_6$ alkyl, in particular, methyl, ethyl, isopropyl, t.-butyl and hexyl.

When $R_1$ is a $C_1$–$C_{20}$ alkyl substituted by $C_2$–$C_5$ alkanoyloxy, $R_1$ is preferably pivaloyloxymethyl.

When $R_4$ and/or $R_5$ are $C_1$–$C_{10}$ alkyl, the alkyl group is preferably $C_1$–$C_4$ alkyl, in particular methyl, ethyl, isopropyl and t.-butyl.

$R_2$ is preferably $C_2$–$C_3$ alkyl, in particular ethyl and propyl or $C_3$ alkenyl, in particular allyl.

When $R_3$ is furyl, thienyl or pyridyl, it is preferably 2-furyl, 2-thienyl or 2-pyridyl.

When $R_8$ is $C_1$–$C_6$ alkyl, it is preferably methyl, ethyl or isopropyl.

Preferably $R_6$ and $R_7$ are independently selected from the group consisting of hydrogen, $C_1$–$C_4$ alkoxy, in particular methoxy or ethoxy, and $C_1$–$C_4$ alkyl, in particular methyl and ethyl.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids.

Preferred salts are the sodium and the potassium salts, as well as the hydrochlorides of the basic esters, e.g. the diethylaminoethyl and dimethylaminoethyl esters.

Particularly preferred compounds of the invention are those of formula (I) wherein $R_1$ is (a'') hydrogen; (b'') $C_1$–$C_6$ alkyl unsubstituted or substituted by a

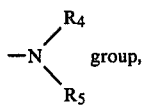

group, wherein each of $R_4$ and $R_5$, which are the same or different, is $C_1-C_4$ alkyl; (c'') 2-(N-pyrrolidinyl)-ethyl; (d'') pivaloyloxymethyl; n is zero or 1; $R_2$ is $C_1-C_4$ alkyl, in particular ethyl or propyl, or $C_3$ alkenyl, in particular allyl; $R_3$ is (a''') phenyl unsubstituted or substituted by $C_1-C_4$ alkyl, in particular methyl or ethyl, or $C_1-C_4$ alkoxy, in particular methoxy; or (b''') 2-furyl, 2-thienyl, 2-pyridyl, the furyl, the thienyl and the pyridyl groups being unsubstituted or substituted by a methyl group, as well as their pharmaceutically acceptable salts.

In the preferred compounds of the invention the —$COOR_1$ group is preferably a free or salified carboxy group.

Examples of particularly preferred compounds of the invention are:

trans 6-carboxy-3-propyl-2-(2-phenyl-cyclopropyl)-chromone;
trans 6-carboxy-3-allyl-2-(2-phenyl-cyclopropyl)-chromone;
trans 6-carboxy-3-ethoxy-2-(2-phenyl-cyclopropyl)-chromone;
trans 6-carboxy-3-butoxy-2-(2-phenyl-cyclopropyl)-chromone;
trans 6-carboxy-3-propyl-2-[2-(2'-methyl-phenyl)-cyclopropyl]-chromone;
trans 6-carboxy-3-allyl-2-[2-(2'-methyl-phenyl)-cyclopropyl]-chromone;
trans 6-carboxy-3-ethoxy-2-[2-(2'-methyl-phenyl)-cyclopropyl]-chromone;
trans 6-carboxy-3-propyl-2-[2-(3'-methyl-phenyl)-cyclopropyl]-chromone;
trans 6-carboxy-3-allyl-2-[2-(3'-methyl-phenyl)-cyclopropyl]-chromone;
trans 6-carboxy-2-propyl-2-[2-(3'-methoxy-phenyl)-cyclopropyl]-chromone;
trans 6-carboxy-3-propyl-2-[2-(2'-methoxy-phenyl)-cyclopropyl]-chromone;
trans 6-carboxy-3-propyl-2-[2-(2'-pyridyl)-cyclopropyl]-chromone;
trans 6-carboxy-3-propyl-2-[2-(5'-methyl-2'-furyl)-cyclopropyl]-chromone;
trans 6-carboxy-3-ethoxy-2-[2-(5'-methyl-2'-furyl)-cyclopropyl]-chromone;
trans 6-carboxy-3-ethyl-2-[2-(2'-methyl-phenyl)-cyclopropyl]-chromone;
trans 6-carboxy-3-propyl-2-[2-(5'-methyl-2'-thienyl)-cyclopropyl]-chromone;
trans 6-carboxy-3-ethoxy-2-[2-(5'-methyl-2'-thienyl)-cyclopropyl]-chromone;
trans 6-carboxy-3-propyl-2-[2-(2'-methyl-phenyl)-cyclopropyl]-chromone 2-diethylaminoethyl ester;
trans 6-carboxy-3-propyl-2-[2-(5'-methyl-2'-furyl)-cyclopropyl]-chromone 2-diethylaminoethyl ester;
trans 6-carboxy-3-propyl-2-[2-(5'-methyl-2'-thienyl)-cyclopropyl]-chromone 2-diethylaminoethyl ester, as well as the pharmaceutically acceptable salts thereof, in particular, the sodium salts and the hydrochlorides of the basic esters (e.g. of those with 2-diethylaminoethanol and 2-dimethylaminoethanol) and the $C_1-C_6$ alkyl esters thereof, in particular the methyl, ethyl, isopropyl, t-butyl and hexyl esters. The compounds of the invention are prepared by a process comprising:

(a) cyclizing a compound of formula (II)

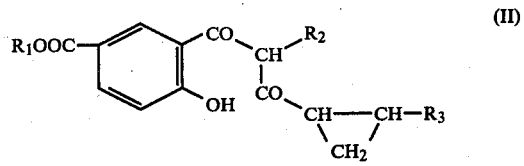

wherein $R_1$, $R_2$ and $R_3$ are as defined above, or a salt thereof, so obtaining compounds of formula (I), wherein n is zero; or (b) cyclopropanating a compound of formula (III)

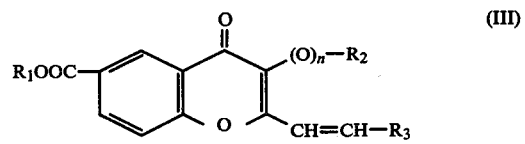

wherein n, $R_1$, $R_2$ and $R_3$ are as defined above, or a salt thereof, and, if desired, converting a compound of formula (I) into another compound of formula (I) by known methods and/or, if desired, converting a compound of formula (I) into a pharmaceutically acceptable salt and/or, if desired, converting a salt into a free compound and/or, if desired, separating a mixture of isomers into the single isomers.

The cyclisation of the compound of formula (II) may be preferably performed in the presence of an acid catalyst, such as, for example, hydrochloric acid, hydroiodic acid, sulphuric acid or formic acid, at a temperature ranging preferably between 20° C. and 120° C.; the cyclisation reaction is preferably carried out in an inert organic solvent selected, e.g., from the group consisting of methanol, ethanol, dioxane, tetrahydrofuran, benzene, toluene, acetic acid and their mixtures.

The cyclopropanation of a compound of the formula (III) may be preferably carried out by reacting a compound of formula (III) with dimethylsulphoxonium methylide (prepared e.g. according to the method described in J. Chem. Soc., 1967, 2495) operating in an inert organic solvent selected e.g. from the group consisting of dimethylformamide, dimethylsulphoxide, dioxane and their mixtures, at a temperature ranging preferably between about 0° C. and about 50°.

A compound of formula (I) may be converted, as stated above, into another compound of formula (I) by known methods; for example, the compound of formula (I) wherein —$COOR_1$ is an esterified carboxy group, may be converted into a compound of formula (I) wherein —$COOR_1$ is carboxy by hydrolysis, e.g. basic hydrolysis, using, for example, sodium or potassium hydroxide, in a solvent, such as, e.g., water or a lower aliphatic alcohol, and operating at a temperature ranging from the room temperature to about 150° C.; the same reaction may be also carried out e.g. by treatment with lithium bromide in dimethylformamide at a temperature higher than 50° C.

In particular a compound of formula (I) wherein —$COOR_1$ is a t-butoxycarbonyl group may be converted into a compound of formula (I) wherein —COOR₁ is carboxy e.g. by treatment with trifluoroacetic acid either in the absence of solvents or in the presence of an inert organic solvent selected e.g. from the group consisting of benzene, toluene, dioxane at a temperature ranging from about 0° C. to about 50° C. or also by treatment, e.g. with trimethylsilyliodide in an inert organic solvent, preferably tetrachloromethane, according to the procedure described in J. Am. Chem. Soc. 99, 968 (1977).

A compound of formula (I) wherein —COOR₁ is carboxy may be converted into a compound of formula (I) wherein —COOR₁ is an esterified carboxy group, e.g. a carbalkoxy group unsubstituted or substituted by C₂-C₅ alkanoyloxy or by a

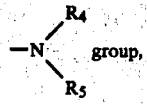
group, wherein R₄ and R₅ are as defined above, by conventional methods, for example by reacting the alkaline salt of the acid with the suitable alkyl halide, in an inert solvent, such as, e.g., acetone, dioxane, dimethylformamide, hexamethylphosphorotriamide at a temperature ranging from about 0° C. to about 100° C.

Alternatively the esterification of a compound of formula (I) may be effected (a) converting the compound of formula (I) wherein —COOR₁ is carboxy into the corresponding halocarbonyl, preferably chlorocarbonyl, derivative, by reaction, e.g., with the desired acid halide, for example oxalyl chloride, thionyl chloride, PCl₃, PCl₅ or POCl₃, either in the absence of solvents or in an inert organic solvent such as, e.g., benzene, toluene, xylene, dioxane, dichloroethane, methylene chloride, tetrahydrofurane, at a temperature ranging preferably from about 0° C. to about 120° C.; and then (b) reacting the obtained halocarbonyl derivative with the suitable alcohol of formula R₁—OH, wherein R₁ is as defined above, in an inert solvent such as, e.g., benzene, toluene, xylene, dioxane, dichloroethane, methylene chloride, tetrahydrofurane, at temperatures varying between about 0° C. and about 120° C., preferably in the presence of a base, such as, e.g., triethylamine or diethylamine.

Also the optional salification of a compound of formula (I) as well as the conversion of a salt into the free compounds and the separation of a mixture of isomers into the single isomers may be carried out by conventional methods. For example, the separation of optical antipodes into the single antipodes may be carried out by salification with an optically active base and by subsequent fractionated crystallization. So the separation of a mixture of cis- and trans-geometric isomers may be carried out for example by fractionated crystallization.

The compounds of formula (II) may be prepared by reacting a compound of formula (IV)

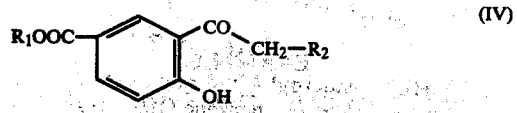 (IV)

wherein
R₁ and R₂ are as defined above, with a compound of formula (V)

 (V)

wherein Z is bromine, chlorine or iodine and

R₃ is as defined above, by conventional methods, e.g., operating in an inert solvent such as benzene, toluene, dioxane, at a temperature ranging from 0° C. to the reflux temperature, in the presence of a basic agent, such as, e.g., pyridine, triethylamine, as acid acceptor, so obtaining a compound of formula (VI)

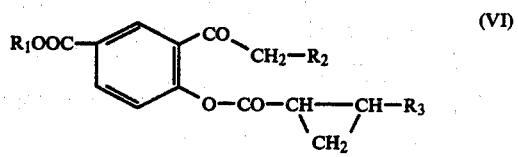 (VI)

wherein

R₁, R₂ and R₃ are as defined above, and then submitting the compound of formula (VI) to a re-arrangement to give the compounds of formula (II); the re-arrangement is preferably carried out in an inert solvent, for example, pyridine, methyl-ethyl-ketone toluene or isopropyl alcohol in the presence of a strong base, e.g., sodium, sodium amide, potassium or sodium hydroxide, or potassium carbonate, at a temperature ranging from the room temperature to the reflux temperature.

The compounds of formula (III) may be prepared, for example, according to the methods described in the German Offenlegungsschrift No. P 27 25 932, corresponding to the Belgian Pat. No. 855,657 and to U.S. applications Nos. 803,947 and 831,467. The compounds of formula (IV) may be prepared, e.g., from the suitable isomer phenoxy derivatives, which are known compounds, by Fries rearrangement.

The compounds of formula (V) are known compounds and can be prepared by conventional methods.

The compounds of the invention own anti-allergic activity, and are therefore useful in the prevention and treatment of all the affections of allergic origin, e.g. bronchial asthma, allergic rhinitis, hay fever, urticaria and dermatosis. The anti-allergic activity of the compounds of the invention is shown, e.g., by the fact that they are active in the passive cutaneous anaphylaxis (PCA) test in rats, according to Goose J. and Blair A.M.J.N. (Immunology, 16, 749, 1969). An important peculiarity of the compounds of the invention is that they exhibit high levels of anti-allergic activity also when orally administered.

The following table shows the activity values obtained in the PCA test in rats, after oral administration, for a number of compounds of this invention, identified by the codes: K 13423, K 13262, K 13449, K 13456, in comparison with the well known anti-allergic drug Disodium Cromoglycate (DSCG).

Activity data are expressed in terms of $K_B$ defined as the dose of active compound capable of reducing to one half the activity of the serum used for the sensitization:

$$K_B = B/(DR-1)$$

wherein

B = dose of antagonist compound expressed in mg/kg;

DR=dose ratio: antilogarithm of the distance between the Log dose effect functions of the serum with and without antagonist (J. H. Gaddum, et al., Exp. Physiol., 1955, 40, 49).

The $K_B$ is adopted here because this value is independent both of the dose of the drug and the reagin concentration used for the sensitization.

The lower the $K_B$ value, the higher the anti-allergic activity. In the following table, the compounds of the invention are identified by the codes:

K 13423=trans 6-carboxy-3-propyl-2-[2-(2'-methylphenyl)-cyclopropyl]-chromone;

K 13262=trans 6-carboxy-3-propyl-2-(2-phenyl-cyclopropyl)-chromone;

K 13449=trans 6-carboxy-3-propyl-2-[2-(3'-methoxyphenyl)-cyclopropyl]-chromone;

K 13456=trans 6-carboxy-3-propyl-2-[2-(5'-methyl-2'-furyl)-cyclopropyl]-chromone.

TABLE

| Compound | Pretreatment time | Anti-allergic activity $K_B$ (mg/kg) - p.o. |
|---|---|---|
| K 13423 | 15' | 0.48 |
| K 13262 | 15' | 4.3 |
| K 13449 | 15' | 4.56 |
| K 13456 | 15' | 5.62 |
| Disodium Cromoglycate | 15' | >200 |

The anti-allergic activity was determined by the inhibition of the lgE-mediated PCA according to Goose J. and Blair A.M.J.N. (loc. cit.) using homocytotropic antibodies raised in rats following the method of Mota I., Immunology, 7, 681, (1964).

The tested compounds were administered per os (p.o.) 15 minutes before the administration of the antigen: at least 6 rats were used for each dose.

Seven days indicative acute toxicity after oral administration was assessed for the compounds of the invention. For example, for the compound identified by the code K 13262, a $LD_{50}$>400 mg/kg in rats was obtained.

The compounds of the present invention furthermore possess anti-ulcer activity, as demonstrated by the fact that they proved to be active in inhibiting stress-induced ulcers in rats undergoing restraint in a water bath at 25° C. for 40 minutes according to a modification of the technique described by Takagi K. and Okabe S. (Jap. J. of Pharmac., 1968, 19: 9). The compounds of the invention own also bronchodilator activity, as shown by the fact that they proved to be active in inhibiting the bronchospasm induced by histamine in guinea-pigs according to the method of Kanzett and Rössler, Arch. Exp. Path. Pharmakol. 71, 195 (1940).

The compounds of the invention may be administered in conventional manner, for instance, orally and parenterally at a daily dosage preferably of 0.5 to 15 mg/kg, or by inhalation, preferably at a daily dosage of 0.5 to 100 mg, preferably 0.5 to 25 mg, or by topical application, e.g. by a cream containing about 0.5-5 mg, preferably 1-2 mg, of the active principle per 100 mg of cream.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners; wetting agents, such as, for instance, lecithin, polisorbates, lauryl-sulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. The compounds of the invention may also be administered in the form of powders by means of a suitable insufflator device and in this case the fine particle sized powders of the active ingredients may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1

Methyl-3-valeroyl-4-hydroxy-benzoate (9 g) dissolved in anhydrous benzene (100 ml) and pyridine (10 ml) was reacted with trans 2-phenyl-cyclopropyl-1-carbonyl chloride at room temperature for 20 hours. The organic solution was washed with diluted HCl, 5%

NaHCO$_3$ and water, then was evaporated to dryness in vacuo to give an oil (17 g) which was dissolved in 2-butanone (150 ml) and reacted with anhydrous K$_2$CO$_3$ (18.6 g) under stirring at reflux temperature for 5 hours. After cooling the reaction mixture was poured in ice-water and extracted with ethyl acetate after neutralization; organic phase was separated and evaporated to dryness in vacuo to give a raw material (15.4 g) which was treated with 99% formic acid (30 ml) at reflux temperature for 30 minutes. After cooling the reaction mixture was poured in ice water and the precipitate was filtered off, washed thoroughly with water and crystallized from ethyl acetate to give trans 6-carbomethoxy-3-propyl-2-(2-phenyl-cyclopropyl)-chromone (6.7 g), m.p. 171°-173° C., which was reacted with 1% KOH in 95% ethanol solution (105 ml) at reflux temperature for 30 minutes. After cooling, the reaction mixture was acidified with 23% HCl, concentrated in vacuo and diluted with ice water: the precipitate was filtered off, washed with water and crystallized from ethyl acetate to give trans 6-carboxy-3-propyl-2-(2-phenyl-cyclopropyl)-chromone (5.4 g), m.p. 195°-196° C.

By proceeding analogously and starting from suitable 3-alkanoyl-4-hydroxy-benzoates, the following compounds were obtained:

trans 6-carboxy-3-methyl-2-(2-phenyl-cyclopropyl)-chromone;
trans 6-carboxy-3-ethyl-2-(2-phenyl-cyclopropyl)-chromone, m.p. 217°-218° C.;
trans 6-carboxy-3-isopropyl-2-(2-phenyl-cyclopropyl)-chromone;
trans 6-carboxy-3-butyl-2-(2-phenyl-cyclopropyl)-chromone, m.p. 198°-199° C.

EXAMPLE 2

By proceeding according to example 1 and starting from suitable trans 2-aryl-cyclopropyl-1-carbonyl-chlorides, the following compounds were prepared:
trans 6-carboxy-3-ethyl-2-[2-(2'-methyl-phenyl)-cyclopropyl]-chromone, m.p. 226°-228° C.;
trans 6-carboxy-3-ethyl-2-[2-(3'-methyl-phenyl)-cyclopropyl]-chromone;
trans 6-carboxy-3-propyl-2-[2-(2'-methyl-phenyl)-cyclopropyl]-chromone, m.p. 206°-207° C.;
trans 6-carboxy-3-propyl-2-[2-(3'-methyl-phenyl)-cyclopropyl]-chromone, m.p. 177°-178° C.;
trans 6-carboxy-3-propyl-2-[2-(4'-methyl-phenyl)-cyclopropyl]-chromone, m.p. 215°-216° C.;
trans 6-carboxy-3-propyl-2-[2-(2'-methoxy-phenyl)-cyclopropyl]-chromone, m.p. 161°-163° C.;
trans 6-carboxy-3-propyl-2-[2-(3'-methoxy-phenyl)-cyclopropyl]-chromone, m.p. 158°-160° C.;
trans 6-carboxy-3-methyl-2-[2-(2'-methyl-phenyl)-cyclopropyl]-chromone;
trans 6-carboxy-3-methyl-2-[2-(4'-methyl-phenyl)-cyclopropyl]-chromone;
trans 6-carboxy-3-methyl-2-[2-(3'-methyl-phenyl)-cyclopropyl]-chromone;
trans 6-carboxy-3-methyl-2-[2-(2'-methoxy-phenyl)-cyclopropyl]-chromone;
trans 6-carboxy-3-methyl-2-[2-(3'-methoxy-phenyl)-cyclopropyl]-chromone;
trans 6-carboxy-3-butyl-2-[2-(2'-methyl-phenyl)-cyclopropyl]-chromone;
trans 6-carboxy-3-butyl-2-[2-(3'-methyl-phenyl)-cyclopropyl]-chromone;
trans 6-carboxy-3-butyl-2-[2-(4'-methyl-phenyl)-cyclopropyl]-chromone;
trans 6-carboxy-3-butyl-2-[2-(2'-methoxy-phenyl)-cyclopropyl]-chromone;
trans 6-carboxy-3-butyl-2-[2-(3'-methoxy-phenyl)-cyclopropyl]-chromone;
trans 6-carboxy-3-ethyl-2-[2-(4'-methyl-phenyl)-cyclopropyl]-chromone;
trans 6-carboxy-3-ethyl-2-[2-(2'-methoxy-phenyl)-cyclopropyl]-chromone.

EXAMPLE 3

By proceeding according to example 1 and starting from suitable trans 2-heteroaryl-cyclopropyl-1-carbonyl chlorides, the following compounds were prepared:
trans 6-carboxy-3-propyl-2-[2-(5'-methyl-2'-furyl)-cyclopropyl]-chromone, m.p. 166°-169° C.;
trans 6-carboxy-3-propyl-2-[2-(5'-methyl-2'-thienyl)-cyclopropyl]-chromone, m.p. 179°-181° C.;
trans 6-carboxy-3-propyl-2-[2-(2'-thienyl)-cyclopropyl]-chromone, m.p. 196°-197° C.

EXAMPLE 4

Trimethyl-sulphoxonium iodide (3.96 g) [J. Chem. Soc., 1967, 2495] was reacted with 50% sodium hydride (0.86 g) in dimethylformamide (40 ml) under stirring at room temperature for 1 hour, then a solution of trans 6-carbomethoxy-3-propyl-2-(2'-methyl-styryl)-chromone (5 g) in dimethylformamide (50 ml) was added. The mixture was allowed to react under stirring at room temperature for 90 minutes, then it was diluted with ice water and extracted with ethyl acetate: organic layer was washed with 5% NaHCO$_3$ and water until neutral. Evaporation to dryness in vacuo and crystallization from methanol gave trans 6-carbomethoxy-3-propyl-2-[2-(2'-methyl-phenyl)-cyclopropyl]-chromone (2.4 g), m.p. 137°-138° C., which was reacted with 1% KOH in 95% ethanol solution (40 ml) at reflux temperature for 30 minutes. After cooling the reaction mixture was acidified with 23% HCl, concentrated in vacuo and diluted with water; the precipitate was filtered and washed with water until neutral. Crystallization from methanol gave trans 6-carboxy-3-propyl-2-[2-(2'-methyl-phenyl)-cyclopropyl]-chromone (1.8 g), m.p. 206°-207° C., I.R.: $\nu$ (C=O) acid 1710, 1690 cm$^{-1}$; $\nu$ (C=O) chromone 1645 cm$^{-1}$.

By proceeding analogously, the following compounds were prepared:
trans 6-carboxy-3-propyl-2-(2-phenyl-cyclopropyl)-chromone, m.p. 195°-196° C.;
trans 6-carboxy-3-propyl-2-[2-(3'-methyl-phenyl)-cyclopropyl]-chromone, m.p. 177°-178° C.;
trans 6-carboxy-3-propyl-2-[2-(4'-methyl-phenyl)-cyclopropyl]-chromone, m.p. 215°-216° C.;
trans 6-carboxy-3-propyl-2-[2-(2'-methoxy-phenyl)-cyclopropyl]-chromone, m.p. 161°-163° C.;
trans 6-carboxy-3-propyl-2-[2-(3'-methoxy-phenyl)-cyclopropyl]-chromone, m.p. 158°-160° C.;
trans 6-carboxy-3-propyl-2-[2-(2'-ethyl-phenyl)-cyclopropyl]-chromone;
trans 6-carboxy-3-propyl-2-[2-(3'-ethoxy-phenyl)-cyclopropyl]-chromone;
trans 6-carboxy-3-propyl-2-[2-(2',5'-dimethyl-phenyl)-cyclopropyl]-chromone;
trans 6-carboxy-3-propyl-2-[2-(2',3'-dimethoxy-phenyl)-cyclopropyl]-chromone;
trans 6-carboxy-3-propyl-2-[2-(2',5'-dimethoxy-phenyl)-cyclopropyl]-chromone;

trans 6-carboxy-3-propyl-2-[2-(2'-methoxy-3'-ethoxy-phenyl)-cyclopropyl]-chromone;
trans 6-carboxy-3-propyl-2-[2-(2'-ethoxy-3'-methoxy-phenyl)-cyclopropyl]-chromone;
trans 6-carboxy-3-propyl-2-[2-(2'-methoxy-5'-methyl-phenyl)-cyclopropyl]-chromone;
trans 6-carboxy-3-propyl-2-[2-(2'-methoxy-3'-methyl-phenyl)-cyclopropyl]-chromone;
trans 6-carboxy-3-allyl-2-(2-phenyl-cyclopropyl)-chromone;
trans 6-carboxy-3-allyl-2-[2-(2'-methyl-phenyl)-cyclopropyl]-chromone, m.p. 189°–190° C.;
trans 6-carboxy-3-allyl-2-[2-(3'-methyl-phenyl)-cyclopropyl]-chromone;
trans 6-carboxy-3-allyl-2-[2-(3'-methoxy-phenyl)-cyclopropyl]-chromone;
trans 6-carboxy-3-ethyl-2-[2-(2'-methyl-phenyl)-cyclopropyl]-chromone, m.p. 226°–228° C.;
trans 6-carboxy-3-ethyl-2-[2-(3'-methyl-phenyl)-cyclopropyl]-chromone;
trans 6-carboxy-3-ethyl-2-[2-(3'-methoxy-phenyl)-cyclopropyl]-chromone;
trans 6-carbomethoxy-3-propyl-2-[2-(3'-methyl-phenyl)-cyclopropyl]-chromone, m.p. 115°–117° C.;
trans 6-carbomethoxy-3-propyl-2-[2-(2'-methoxy-phenyl)-cyclopropyl]-chromone, m.p. 125°–127° C.

EXAMPLE 5

Trimethyl-sulphoxonium iodide (2.86 g) was reacted with 50% sodium hydride (0.62 g) in dimethylformamide (30 ml) under stirring at room temperature for 2 hours, then a solution of trans 6-carbomethoxy-3-propyl-2-[2-(5'-methyl-2'-furyl)-vinyl]-chromone (3.52 g) in dimethylformamide (30 ml) was added. The mixture was allowed to react under stirring at room temperature for 90 minutes, then it was diluted with ice water, acidified with 2 N HCl and extracted with ethyl acetate: organic layer was washed with 5% NaHCO$_3$ and water until neutral. Evaporation to dryness in vacuo and crystallization from methanol gave trans 6-carbomethoxy-3-propyl-2-[2-(5'-methyl-2'-furyl)-cyclopropyl]-chromone (2.2 g), m.p. 138°–139° C., which was reacted with 1% KOH in 95% ethanol solution (40 ml) at reflux temperature for 30 minutes. After cooling the reaction mixture was acidified with 10% NaH$_2$PO$_4$, concentrated in vacuo and diluted with water: the precipitate was filtered off and washed with water. Crystallization from isopropanol gave trans 6-carboxy-3-propyl-2-[2-(5'-methyl-2'-furyl)-cyclopropyl]-chromone (1.5 g), m.p. 166°–169° C.

By proceeding analogously, the following compounds were prepared:
trans 6-carbomethoxy-3-propyl-2-[2-(5'-methyl-2'-thienyl)-cyclopropyl]-chromone, m.p. 151°–153° C.;
trans 6-carboxy-3-propyl-2-[2-(5'-methyl-2'-thienyl)-cyclopropyl]-chromone, m.p. 179°–181° C.;
trans 6-carbomethoxy-3-propyl-2-[2-(2'-thienyl)-cyclopropyl]-chromone, m.p. 159°–161° C.;
trans 6-carboxy-3-propyl-2-[2-(2'-thienyl)-cyclopropyl]-chromone, m.p. 196°–197° C.;
trans 6-carbomethoxy-3-propyl-2-[2-(2'-pyridyl)-cyclopropyl]-chromone, m.p. 180°–182° C.;
trans 6-carboxy-3-propyl-2-[2-(2'-pyridyl)-cyclopropyl]-chromone, m.p. 209°–210° C.;
trans 6-carboxy-3-ethyl-2-[2-(5'-methyl-2'-furyl)-cyclopropyl]-chromone;
trans 6-carboxy-3-ethyl-2-[2-(5'-methyl-2'-thienyl)-cyclopropyl]-chromone;
trans 6-carboxy-3-allyl-2-[2-(5'-methyl-2'-furyl)-cyclopropyl]-chromone;
trans 6-carboxy-3-allyl-2-[2-(5'-methyl-2'-thienyl)-cyclopropyl]-chromone;
trans 6-carboxy-3-ethyl-2-[2-(2'-thienyl)-cyclopropyl]-chromone;
trans 6-carboxy-3-ethyl-2-[2-(2'-pyridyl)-cyclopropyl]-chromone.

EXAMPLE 6

Trimethyl-sulphoxonium iodide (2.86 g) was reacted with 50% sodium hydride (0.62 g) in dimethylformamide (50 ml) under stirring at room temperature for 1 hour, then a solution of trans 6-carboxy-3-propyl-2-(2'-methyl-styryl)-chromone sodium salt (3.7 g) in dimethylformamide (50 ml) was added. The mixture was allowed to react under stirring at room temperature for 18 hours, then it was diluted with ice water and acidified with 23% HCl: the precipitate was filtered off and washed with water until neutral. Crystallization from methanol gave trans 6-carboxy-3-propyl-2-[2-(2'-methyl-phenyl)-cyclopropyl]-chromone (1.85 g), m.p. 206°–207° C.

By proceeding analogously, the following compounds were prepared:
trans 6-carboxy-3-propyl-2-[2-(3'-methyl-phenyl)-cyclopropyl]-chromone, m.p. 177°–178° C.;
trans 6-carboxy-3-propyl-2-[2-(2'-methoxy-phenyl)-cyclopropyl]-chromone; m.p. 161°–163° C.;
trans 6-carboxy-3-propyl-2-[2-(3'-methoxy-phenyl)-cyclopropyl]-chromone, m.p. 158°–160° C.;
trans 6-carboxy-3-allyl-2-[2-(2'-methoxy-phenyl)-cyclopropyl]-chromone.

EXAMPLE 7

By proceeding according to example 6, the following compounds were prepared:
trans 6-carboxy-3-propyl-2-[2-(5'-methyl-3'-furyl)-cyclopropyl]-chromone, m.p. 166°–169° C.;
trans 6-carboxy-3-propyl-2-[2-(5'-methyl-2'-thienyl)-cyclopropyl]-chromone, m.p. 179°–181° C.

EXAMPLE 8

By proceeding according to examples 4 and 5, starting from the suitable trans 6-carboxy-3-propyl-2-substituted-chromones t-butyl-esters, the following compounds were obtained:
trans 6-carboxy-3-propyl-2-[2-(2'-methyl-phenyl)-cyclopropyl]-chromone t-butyl-ester, oil, I.R.: $\nu$ (C=O) ester 1710 cm$^{-1}$; $\nu$ (C=O) chromone 1640 cm$^{-1}$;
trans 6-carboxy-3-propyl-2-[2-(3'-methyl-phenyl)-cyclopropyl]-chromone t-butyl-ester;
trans 6-carboxy-3-propyl-2-[2-(3'-methoxy-phenyl)-cyclopropyl]-chromone t-butyl-ester;
trans 6-carboxy-3-propyl-2-[2-(2'-methoxy-phenyl)-cyclopropyl]-chromone t-butyl-ester;
trans 6-carboxy-3-propyl-2-[2-(5'-methyl-2'-furyl)-cyclopropyl]-chromone t-butyl-ester, oil, I.R.: $\nu$ (C=O) ester 1720 cm$^{-1}$, $\nu$ (C=O) chromone 1645 cm$^{-1}$;
trans 6-carboxy-3-propyl-2-[2-(5'-methyl-2'-thienyl)-cyclopropyl]-chromone t-butyl-ester.

EXAMPLE 9

Trans 6-carboxy-3-propyl-2-[2-(2'-methyl-phenyl)-cyclopropyl]-chromone t-butyl-ester (4.3 g) was reacted with trifluoroacetic acid (30.2 ml) at room temperature for 6 hours. Trifluoroacetic acid was evaporated in vacuo and the residue was diluted with ice water: the precipitate was filtered off and washed with water until neutral. Crystallization from ethanol gave trans 6-carboxy-3-propyl-2-[2-(2'-methyl-phenyl)-cyclopropyl]-chromone (3.2 g), m.p. 206°–207° C.

By proceeding analogously, the following compounds were prepared:
trans 6-carboxy-3-allyl-2-[2-(4'-methyl-phenyl)-cyclopropyl]-chromone;
trans 6-carboxy-3-propyl-2-[2-(3'-methoxy-phenyl)-cyclopropyl]-chromone, m.p. 158°–160° C.;
trans 6-carboxy-3-propyl-2-[2-(2'-methoxy-phenyl)-cyclopropyl]-chromone, m.p. 161°–163° C.

EXAMPLE 10

Trans 6-carboxy-3-propyl-2-[2-(5'-methyl-2'-furyl)-cyclopropyl]-chromone t-butyl-ester (4.25 g) was treated with trimethylsilyl iodide (2 g=1.42 ml) in carbon tetrachloride (50 ml), under nitrogen, with stirring at room temperature for 2 hours and then at 50° C. for 2 hours. After cooling the reaction mixture was diluted with ethyl ether and extracted with 2% NaHCO$_3$: the aqueous layer was separated and acidified with 23% HCl. The precipitate was filtered off and washed with water until neutral.

Crystallization from isopropyl alcohol gave trans 6-carboxy-3-propyl-2-[2-(5'-methyl-2'-furyl)-cyclopropyl]-chromone (2.35 g), m.p. 166°–169° C.

By proceeding analogously, the following compound was prepared:
trans 6-carboxy-3-propyl-2-[2-(5'-methyl-2'-thienyl)-cyclopropyl]-chromone, m.p. 179°–181° C.

EXAMPLE 11

By proceeding according to examples 4, 6, 8, 9, starting from the suitable trans 6-carboxy- and trans 6-carbalkoxy-3-alkoxy-2-styryl-chromones, the following compounds were prepared:
trans 6-carboxy-3-ethoxy-2-(2-phenyl-cyclopropyl)-chromone, m.p. 178°–180° C.;
trans 6-carboxy-3-butoxy-2-(2-phenyl-cyclopropyl)-chromone;
trans 6-carboxy-3-ethoxy-2-[2-(2'-methyl-phenyl)-cyclopropyl]-chromone, m.p. 207°–208° C.;
trans 6-carboxy-3-ethoxy-2-[2-(3'-methyl-phenyl)-cyclopropyl]-chromone;
trans 6-carboxy-3-ethoxy-2-[2-(4'-methyl-phenyl)-cyclopropyl]-chromone;
trans 6-carboxy-3-ethoxy-2-[2-(3'-methoxy-phenyl)-cyclopropyl]-chromone;
trans 6-carboxy-3-ethoxy-2-[2-(2'-methoxy-phenyl)-cyclopropyl]-chromone.

EXAMPLE 12

By proceeding according to examples 5, 7, 8 and 10, starting from the suitable trans 6-carboxy- and trans 6-carbalkoxy-3-alkoxy-2-(2-heteroaryl-vinyl)-chromones, the following compounds were prepared:
trans 6-carboxy-3-ethoxy-2-[2-(5'-methyl-2'-furyl)-cyclopropyl]-chromone, m.p. 145°–146° C.;
trans 6-carboxy-3-ethoxy-2-[2-(5'-methyl-2'-thienyl)-cyclopropyl]-chromone;
trans 6-carboxy-3-ethoxy-2-[2-(2'-thienyl)-cyclopropyl]-chromone;
trans 6-carboxy-3-ethoxy-2-[2-(2'-pyridyl)-cyclopropyl]-chromone.

EXAMPLE 13

Trans 6-carboxy-3-propyl-2-[2-(2'-methyl-phenyl)-cyclopropyl]-chromone (8 g) was reacted with ethyl iodide (5.4 g) and anhydrous K$_2$CO$_3$ (6.3 g) in dimethylformamide (70 ml) under stirring at room temperature for 4 hours. After dilution with ice water the precipitate was filtered off and crystallized from isopropyl ether: trans 6-carboxy-3-propyl-2-[2-(2'-methyl-phenyl)-cyclopropyl]-chromone ethyl-ester (7.8 g), m.p. 118°–120° C., was obtained.

By proceeding analogously, the following compounds were prepared:
trans 6-carboxy-3-propyl-2-(2-phenyl-cyclopropyl)-chromone ethyl-ester;
trans 6-carboxy-3-propyl-2-[2-(3'-methyl-phenyl)-cyclopropyl]-chromone ethyl-ester;
trans 6-carboxy-3-propyl-2-[2-(3'-methoxy-phenyl)-cyclopropyl]-chromone ethyl-ester;
trans 6-carboxy-3-propyl-2-[2-(2'-methoxy-phenyl)-cyclopropyl]-chromone ethyl-ester;
trans 6-carboxy-3-allyl-2-(2-phenyl-cyclopropyl)-chromone ethyl-ester;
trans 6-carboxy-3-allyl-2-[2-(2'-methyl-phenyl)-cyclopropyl]-chromone ethyl ester;
trans 6-carboxy-3-ethoxy-2-(2-phenyl-cyclopropyl)-chromone ethyl-ester;
trans 6-carboxy-3-ethoxy-2-[2-(4'-methyl-phenyl)-cyclopropyl]-chromone ethyl-ester;
trans 6-carboxy-3-ethyl-2-[2-(2'-methyl-phenyl)-cyclopropyl]-chromone ethyl-ester;
trans 6-carboxy-3-propyl-2-[2-(5'-methyl-2'-furyl)-cyclopropyl]-chromone ethyl-ester, m.p. 76°–78° C.;
trans 6-carboxy-3-propyl-2-[2-(5'-methyl-2'-thienyl)-cyclopropyl]-chromone ethyl-ester;
trans 6-carboxy-3-propyl-2-[2-(2'-thienyl)-cyclopropyl]-chromone ethyl-ester;
trans 6-carboxy-3-ethoxy-2-[2-(5'-methyl-2'-thienyl)-cyclopropyl]-chromone ethyl-ester;
trans 6-carboxy-3-ethoxy-2-[2-(5'-methyl-2'-furyl)-cyclopropyl]-chromone ethyl ester;
trans 6-carboxy-3-allyl-2-[2-(3'-methyl-phenyl)-cyclopropyl]-chromone ethyl-ester;
trans 6-carboxy-3-ethoxy-2-[2-(2'-methyl-phenyl)-cyclopropyl]-chromone ethyl-ester;
trans 6-carboxy-3-ethyl-2-[2-(5'-methyl-2'-furyl)-cyclopropyl]-chromone ethyl-ester.

EXAMPLE 14

By proceeding according to example 13 the isopropyl, n-1-hexyl and n-1-octyl esters of the following compounds were prepared:
trans 6-carboxy-3-propyl-2-(2-phenyl-cyclopropyl)-chromone;
trans 6-carboxy-3-propyl-2-[2-(2'-methyl-phenyl)-cyclopropyl]-chromone;
trans 6-carboxy-3-propyl-2-[2-(3'-methyl-phenyl)-cyclopropyl]-chromone;
trans 6-carboxy-3-propyl-2-[2-(5'-methyl-2'-furyl)-cyclopropyl]-chromone;
trans 6-carboxy-3-propyl-2-[2-(5'-methyl-2'-thienyl)-cyclopropyl]-chromone;
trans 6-carboxy-3-allyl-2-[2-(2'-methyl-phenyl)-cyclopropyl]-chromone;
trans 6-carboxy-3-allyl-2-[2-(3'-methyl-phenyl)-cyclopropyl]-chromone;;
trans 6-carboxy-3-ethoxy-2-(2-phenyl-cyclopropyl)-chromone;

trans 6-carboxy-3-ethoxy-2-[2-(4'-methyl-phenyl)-cyclopropyl]-chromone;
trans 6-carboxy-3-ethoxy-2-[2-(5'-methyl-2'-furyl)-cyclopropyl]-chromone;
trans 6-carboxy-3-propyl-2-[2-(2'-methoxy-phenyl)-cyclopropyl]-chromone;
trans 6-carboxy-3-propyl-2-[2-(3'-methoxy-phenyl)-cyclopropyl]-chromone;
trans 6-carboxy-3-ethyl-2-[2-(5'-methyl-2'-furyl)-cyclopropyl]-chromone;
trans 6-carboxy-3-ethyl-2-[2-(2'-methyl-phenyl)-cyclopropyl]-chromone.

EXAMPLE 15

Trans 6-carboxy-3-propyl-2-[2-(2'-methyl-phenyl)-cyclopropyl]-chromone (5 g) was reacted with chloromethylpivalate (5 ml) and triethylamine (2 ml) in dimethylformamide (40 ml) at 70° C. for 2 hours. After cooling the mixture was diluted with ice water and extracted with ethyl acetate: organic layer was washed with 5% NaHCO$_3$ and water. After evaporation in vacuo to dryness, the residue was crystallized from isopropyl ether: trans 6-carboxy-3-propyl-2-[2-(2'-methyl-phenyl)-cyclopropyl]-chromone pivaloyloxymethyl-ester (3.65 g), I.R.: $\nu$ (C=O) ester 1735 cm$^{-1}$, $\nu$ (C=O) chromone 1640 cm$^{-1}$, was obtained.

By proceeding analogously, the pivaloyloxy-methyl-esters of the following compounds were prepared:
trans 6-carboxy-3-propyl-2-(2-phenyl-cyclopropyl)-chromone;
trans 6-carboxy-3-propyl-2-[2-(3'-methyl-phenyl)-cyclopropyl]-chromone;
trans 6-carboxy-3-propyl-2-[2-(2'-methoxy-phenyl)-cyclopropyl]-chromone;
trans 6-carboxy-3-propyl-2-[2-(3'-methoxy-phenyl)-cyclopropyl]-chromone;
trans -6-carboxy-3-propyl-2-[2-(5'-methyl-2'-furyl)-cyclopropyl]-chromone;
trans 6-carboxy-3-propyl-2-[2-(5'-methyl-2'-thienyl)-cyclopropyl]-chromone;
trans 6-carboxy-3-allyl-2-(2-phenyl-cyclopropyl)-chromone;
trans 6-carboxy-3-allyl-b 2-[2-(2'-methyl-phenyl)-cyclopropyl]-chromone;
trans 6-carboxy-3-ethoxy-2-(2-phenyl-cyclopropyl)-chromone;
trans 6-carboxy-3-ethoxy-2-[2-(5'-methyl-2'-furyl)-cyclopropyl]-chromone;
trans 6-carboxy-3-ethyl-2-[2-(5'-methyl-2'-furyl)-cyclopropyl]-chromone;
trans 6-carboxy-3-ethyl-2-[2-(2'-methyl-phenyl)-cyclopropyl]-chromone.

EXAMPLE 16

Trans 6-carboxy-3-propyl-2-[2-(2'-methyl-phenyl)-cyclopropyl]-chromone (3.6 g) was reacted with 1-chloro-2-diethylamino-ethane (2.7 g) and anhydrous K$_2$CO$_3$ (2.8 g) in dimethylformamide (40 ml) under stirring at 20° C. for 8 hours. After dilution with water, the precipitate was filtered off and washed with water until neutral: crystallization from isopropyl ether gave trans 6-carboxy-3-propyl-2-[2-(2'-methyl-phenyl)-cyclopropyl]-chromone 2-diethylaminoethylester (2.2 g), m.p. 89°–90° C.

By proceeding analogously, the following compounds were prepared:
trans 6-carboxy-3-propyl-2-[2-(3'-methyl-phenyl)-cyclopropyl]-chromone 2-diethylaminoethyl-ester;
trans 6-carboxy-3-propyl-2-[2-(2'-methoxy-phenyl)-cyclopropyl]chromone 2-diethylaminoethyl-ester;
trans 6-carboxy-3-propyl-2-[2-(3'-methoxy-phenyl)-cyclopropyl]-chromone 2-diethylaminoethyl-ester;
trans 6-carboxy-3-propyl-2-[2-(5'-methyl-2'-furyl)-cyclopropyl]-chromone 2-diethylaminoethyl-ester;
trans 6-carboxy-3-propyl-2-[2-(5'-methyl-2'-thienyl)-cyclopropyl]-chromone 2-diethylaminoethyl-ester;
trans 6-carboxy-3-allyl-2-[2-(2'-methyl-phenyl)-cyclopropyl]-chromone 2-diethylaminoethyl-ester;
trans 6-carboxy-3-ethoxy-2-(2-phenyl-cyclopropyl)-chromone 2-diethylaminoethyl-ester;
trans 6-carboxy-3-ethoxy-2-[2-(5'-methyl-2'-furyl)-cyclopropyl]-chromone 2-diethylaminoethyl-ester.

EXAMPLE 17

Trans 6-carboxy-3-propyl-2-[2-(2'-methyl-phenyl)-cyclopropyl]-chromone (12 g) was reacted with thionyl chloride (6 ml) in dioxane (120 ml) at room temperature for 3 hours, then the mixture was evaporated to dryness in vacuo. The residue was dissolved in dioxane (80 ml) and triethylamine (2 ml) and was reacted with 2-diethylamino-ethanol (4 ml) at room temperature for 20 hours. After dilution with water the precipitate was filtered off, dissolved in ethyl ether (100 ml) and treated with the stoichiometric amount of HCl in ether: the precipitate was filtered off, washed with ethyl ether and dissolved in water. Alkalinization with K$_2$CO$_3$ and filtration gave trans 6-carboxy-3-propyl-2-[2-(2'-methyl-phenyl)-cyclopropyl]-chromone 2-diethylaminoethyl-ester (7.8 g), m.p. 89°–90° C.; I.R.: $\nu$ (C=O) ester 1720 cm$^{-1}$, $\nu$ (C=O) chromone 1640–1610 cm$^{-1}$.

By proceeding analogously, the following compounds were prepared:
trans 6-carboxy-3-propyl-2-(2-phenyl-cyclopropyl)-chromone 2-diethylaminoethyl-ester;
trans 6-carboxy-3-propyl-2-[2-(3'-methyl-phenyl)-cyclopropyl]-chromone 2-diethylaminoethyl-ester;
trans 6-carboxy-3-allyl-2-[2-(3'-methyl-phenyl)-cyclopropyl]-chromone 2-diethylaminoethyl-ester;
trans 6-carboxy-3-ethoxy-2-[2-(4'-methyl-phenyl)-cyclopropyl]-chromone 2-diethylaminoethyl-ester.

EXAMPLE 18

Trimethyl-sulphoxonium iodide (2.3 g) was reacted with 50% sodium hydride (0.5 g) in dimethylformamide (30 ml) under stirring at room temperature for 1 hour, then a solution of trans 6-carboxy-3-propyl-2-styryl-chromone 2diethylaminoethyl-ester (3.5 g) in dimethylformamide (20 ml) was added. The mixture was allowed to react under stirring at room temperature for 90 minutes, then it was diluted with water and extracted with ethyl acetate: organic layer was washed with water and evaporated to dryness in vacuo. The residue (2.9 g) was purified by column chromatography over SiO$_2$ using a mixture benzene-ethyl acetate-triethylamine 90:10:0.2 as eluent. Trans 6-carboxy-3-propyl-2-(2-phenyl-cyclopropyl)-chromone 2-diethylaminoethyl ester (1.7 g), m.p. 92°–94° C. was obtained.

By proceeding analogously, the following compounds were prepared:
trans 6-carboxy-3-ethyl-2-[2-(5'-methyl-2'-furyl)-cyclopropyl]-chromone 2-diethylaminoethyl-ester;
trans 6-carboxy-3-propyl-2-[2-(2'-methyl-phenyl)-cyclopropyl]-chromone 2-diethylaminoethyl-ester, m.p. 89°–90° C.;
trans 6-carboxy-3-propyl-2-[2-(5'-methyl-2'-furyl)-cyclopropyl]-chromone 2-diethylaminoethyl-ester;

trans 6-carboxy-3-ethyl-2-[2-(2'-methyl-phenyl)-cyclopropyl]-chromone 2-diethylaminoethyl-ester;
trans 6-carboxy-3-ethoxy-2-[2-(2'-methyl-phenyl)-cyclopropyl]-chromone 2-diethylaminoethyl-ester;
trans 6-carboxy-3-allyl-2-(2-phenyl-cyclopropyl)-chromone 2-diethylaminoethyl-ester.

EXAMPLE 19

By proceeding according to examples 16, 17 and 18, the 2-dimethylaminoethyl-esters and the 2-(N-pirrolidinyl)-ethyl-esters of the following compounds were prepared:
trans 6-carboxy-3-propyl-2-(2-phenyl-cyclopropyl)-chromone;
trans 6-carboxy-3-allyl-2-(2-phenyl-cyclopropyl)-chromone;
trans 6-carboxy-3-ethoxy-2-(2-phenyl-cyclopropyl)-chromone;
trans 6-carboxy-3-propyl-2-[2-(2'-methyl-phenyl)-cyclopropyl]-chromone;
trans 6-carboxy-3-propyl-2-[2-(3'-methyl-phenyl)-cyclopropyl]-chromone;
trans 6-carboxy-3-ethyl-2-(2-phenyl-cyclopropyl)-chromone;
trans 6-carboxy-3-butyl-2-(2-phenyl-cyclopropyl)-chromone;
trans 6-carboxy-3-propyl-2-[2-(5'-methyl-2'-furyl)-cyclopropyl]-chromone;
trans 6-carboxy-3-propyl-2-[2-(5'-methyl-2'-thienyl)-cyclopropyl]-chromone;
trans 6-carboxy-3-allyl-2-[2-(2'-methyl-phenyl)-cyclopropyl]-chromone;
trans 6-carboxy-3-allyl-2-[2-(3'-methyl-phenyl)-cyclopropyl]-chromone;
trans 6-carboxy-3-ethoxy-2-[2-(4'-methyl-phenyl)-cyclopropyl]-chromone;
trans 6-carboxy-3-ethoxy-2-[2-(2'-methyl-phenyl)-cyclopropyl]-chromone;
trans 6-carboxy-3-ethoxy-2-[2-(5'-methyl-2'-furyl)-cyclopropyl]-chromone;
trans 6-carboxy-3-propyl-2-[2-(2'-methoxy-phenyl)-cyclopropyl]-chromone;
trans 6-carboxy-3-propyl-2-[2-(3'-methoxy-phenyl)-cyclopropyl]-chromone;
trans 6-carboxy-3-ethyl-2-[2-(5'-methyl-2'-furyl)-cyclopropyl]-chromone;
trans 6-carboxy-3-ethyl-2-[2-(2'-methyl-phenyl)-cyclopropyl]-chromone.

EXAMPLE 20

Trans 6-carboxy-3-propyl-2-[2-(2'-methyl-phenyl)-cyclopropyl]-chromone (5.15 g) was reacted with NaHCO$_3$ (1.25 g) in water (30 ml) at 100° C. until the solution was completed. After cooling to 5° C. a precipitate was obtained, which was filtered off and washed with ice water. Trans 6-carboxy-3-propyl-2-[2-(2'-methyl-phenyl)-cyclopropyl]-chromone sodium salt (4.3 g) was obtained.

By proceeding analogously the sodium salts of the acids listed in the example 19 were prepared.

EXAMPLE 21

Trans 6-carboxy-3-propyl-2-[2-(2'-methyl-phenyl)-cyclopropyl]-chromone (3.6 g) was reacted with N-methyl-N-benzyl-amine (1.6 g) under stirring at 120° C. for 30 minutes. After cooling ethyl acetate was added so as to obtain a crystalline precipitate which was filtered and washed with ethyl acetate. Trans 6-carboxy-3-propyl-2-[2-(2'-methyl-phenyl)-cyclopropyl]-chromone N-methyl-N-benzyl-ammonium salt (4.15 g) was obtained.

By proceeding analogously the N-methyl-N-benzyl-ammonium salts of the acids listed in the example 19 were prepared.

EXAMPLE 22

By proceeding according to example 21, the salts with triethylamine, triethanolamine, N-ethyl-piperidine, N-ethylmorpholine, N,N-diethylamino-ethylamine, β-phenethylamine of the acids listed in the example 19 were prepared.

EXAMPLE 23

By proceeding according to examples 3 and 5, the following compounds were prepared:
trans 6-carboxy-3-methyl-2-[2-(2'-pyridyl)-cyclopropyl]-chromone;
trans 6-carboxy-3-butyl-2-[2-(2'-pyridyl)-cyclopropyl]-chromone;
trans 6-carboxy-3-methyl-2-[2-(2'-thienyl)-cyclopropyl]-chromone;
trans 6-carboxy-3-butyl-2-[2-(2'-thienyl)-cyclopropyl]-chromone;
trans 6-carboxy-3-methyl-2-[2-(5'-methyl-2'-furyl)-cyclopropyl]-chromone;
trans 6-carboxy-3-butyl-2-[2-(5'-methyl-2'-furyl)-cyclopropyl]-chromone;
trans 6-carboxy-3-methyl-2-[2-(5'-methyl-2'-thienyl)-cyclopropyl]-chromone;
trans 6-carboxy-3-butyl-2-[2-(5'-methyl-2'-thienyl)-cyclopropyl]-chromone.

EXAMPLE 24

By proceeding according to examples 13 and 14, the following compounds were prepared:
trans 6-carboxy-3-ethyl-2-(2-phenyl-cyclopropyl)-chromone ethyl-ester;
trans 6-carboxy-3-butyl-2-(2-phenyl-cyclopropyl)-chromone ethyl-ester;
trans 6-carboxy-3-propyl-2-[2-(4'-methyl-phenyl)-cyclopropyl]-chromone ethyl ester;
trans 6-carboxy-3-ethyl-2-(2-phenyl-cyclopropyl)-chromone isopropyl-ester;
trans 6-carboxy-3-ethyl-2-(2-phenyl-cyclopropyl)-chromone (1-hexyl)-ester;
trans 6-carboxy-3-ethyl-2-(2-phenyl-cyclopropyl)-chromone (1-octyl)-ester;
trans 6-carboxy-3-allyl-2-(2-phenyl-cyclopropyl)-chromone isopropyl-ester;
trans 6-carboxy-3-allyl-2-(2-phenyl-cyclopropyl)-chromone (1-hexyl)-ester;
trans 6-carboxy-3-allyl-2-(2-phenyl-cyclopropyl)-chromone (1-octyl)-ester;
trans 6-carboxy-3-propyl-2-[2-(4'-methyl-phenyl)-cyclopropyl]-chromone isopropyl-ester;
trans 6-carboxy-3-propyl-2-[2-(4'-methyl-phenyl)-cyclopropyl]-chromone (1-hexyl)-ester;
trans 6-carboxy-3-propyl-2-[2-(4'-methyl-phenyl)-cyclopropyl]-chromone (1-octyl)-ester;
trans 6-carboxy-3-propyl-2-[2-(2'-pyridyl)-cyclopropyl]-chromone ethyl-ester;
trans 6-carboxy-3-propyl-2-[2-(2'-thienyl)-cyclopropyl]-chromone isopropyl-ester;
trans 6-carboxy-3-propyl-2-[2-(2'-thienyl)-cyclopropyl]-chromone (1-hexyl)-ester;

trans 6-carboxy-3-propyl-2-[2-(2'-thienyl)-cyclopropyl]-chromone (1-octyl)-ester;
trans 6-carboxy-3-ethoxy-2-[2-(5'-methyl-2'-thienyl)-cyclopropyl]-chromone isopropyl ester;
trans 6-carboxy-3-ethoxy-2-[2-(5'-methyl-2'-thienyl)-cyclopropyl]-chromone (1-hexyl)-ester;
trans 6-carboxy-3-ethoxy-2-[2-(5'-methyl-2'-thienyl)-cyclopropyl]-chromone (1-octyl)-ester.

EXAMPLE 25

By proceeding according to example 19, the 2-dimethylaminoethyl-esters and the 2-(N-pyrrolidinyl)-ethyl-esters of the following compounds were prepared:
trans 6-carboxy-3-ethyl-2-[2-(3'-methyl-phenyl)-cyclopropyl]-chromone;
trans 6-carboxy-3-ethoxy-2-[2-(3'-methyl-phenyl)-cyclopropyl]-chromone;
trans 6-carboxy-3-propyl-2-[2-(4'-methyl-phenyl)-cyclopropyl]-chromone;
trans 6-carboxy-3-propyl-2-[2-(2'-thienyl)-cyclopropyl]-chromone;
trans 6-carboxy-3-ethoxy-2-[2-(5'-methyl-2'-thienyl)-cyclopropyl]-chromone.

EXAMPLE 26

By proceeding according to examples 16 and 18, the 2-diethylaminoethyl-esters of the following compounds were prepared:
trans 6-carboxy-3-ethyl-2-[2-(2'-thienyl)-cyclopropyl]-chromone;
trans 6-carboxy-3-propyl-2-[2-(2'-thienyl)-cyclopropyl]-chromone;
trans 6-carboxy-3-propyl-2-[2-(2'-pyridyl)-cyclopropyl]-chromone;
trans 6-carboxy-3-ethoxy-2-[2-(5'-methyl-2'-furyl)-cyclopropyl]-chromone;
trans 6-carboxy-3-ethoxy-2-[2-(5'-methyl-2'-thienyl)-cyclopropyl]-chromone.

EXAMPLE 27

By proceeding according to example 15, the following compounds were prepared:
trans 6-carboxy-3-propyl-2-[2-(2'-thienyl)-cyclopropyl]-chromone pivaloyloxymethyl-ester;
trans 6-carboxy-3-ethoxy-2-[2-(5'-methyl-2'-thienyl)-cyclopropyl]-chromone pivaloyloxymethyl-ester.

EXAMPLE 28

By proceeding according to examples 1, 4 and 6, starting from the suitable cis-derivatives, the following compounds were prepared:
cis 6-carboxy-3-ethyl-2-(2-phenyl-cyclopropyl)-chromone;
cis 6-carboxy-3-propyl-2-(2-phenyl-cyclopropyl)-chromone;
cis 6-carboxy-3-allyl-2-(2-phenyl-cyclopropyl)-chromone;
cis 6-carboxy-3-ethoxy-2-(2-phenyl-cyclopropyl)-chromone;
cis 6-carboxy-3-ethyl-2-[2-(2'-methyl-phenyl)-cyclopropyl]-chromone;
cis 6-carboxy-3-propyl-2-[2-(2'-methyl-phenyl)-cyclopropyl]-chromone;
cis 6-carboxy-3-allyl-2-[2-(2'-methyl-phenyl)-cyclopropyl]-chromone;
cis 6-carbosy-3-ethoxy-2-[2-(2'-methyl-phenyl)-cyclopropyl]-chromone;
cis 6-carboxy-3-ethyl-2-[2-(4'-methyl-phenyl)-cyclopropyl]-chromone;
cis 6-carboxy-3-propyl-2-[2-(4'-methyl-phenyl)-cyclopropyl]-chromone;
cis 6-carboxy-3-allyl-2-[2-(4'-methyl-phenyl)-cyclopropyl]-chromone;
cis 6-carboxy-3-ethoxy-2-[2-(4'-methyl-phenyl)-cyclopropyl]-chromone.

EXAMPLE 29

Tablets, each weighing 150 mg and containing 50 mg of the active substance are manufactured as follows:

Composition (for 10,000 tablets)

| | |
|---|---|
| trans 6-carboxy-3-propyl-2-[2-(2'-methyl-phenyl)-cyclopropyl]-chromone | 500 g |
| lactose | 710 g |
| corn starch | 237.5 g |
| talc powder | 37.5 g |
| magnesium stearate | 15 g | trans 6-carboxy-3-propyl-2-[2-(2'-methyl-phenyl)-cyclopropyl]-chromone, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

EXAMPLE 30

Aerosol formulation:

| | |
|---|---|
| trans 6-carboxy-3-propyl-2-[2-(2'-methyl-phenyl)-cyclopropyl]-chromone | 2% |
| ethanol | 10% |
| lecithin | 0.2% |
| mixture of dichlorodifluoromethane and dichlorotetrafluoroethane (70:30 mixture) | ad 100% |

We claim:
1. A compound of formula (I)

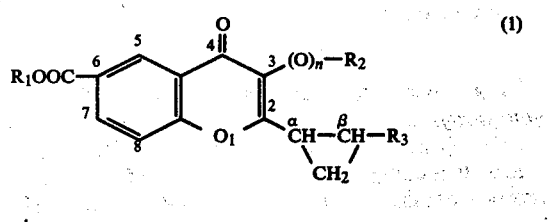

wherein
n is zero or 1;
R₁ is hydrogen or $C_1$–$C_{20}$ alkyl, unsubstituted or substituted by a $C_2$–$C_5$ alkanoyloxy or by a

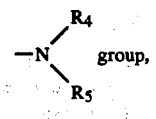

group, wherein each of R₄ and R₅ is independently selected from the group consisting of hydrogen and $C_1$–$C_{10}$ alkyl, or R₄ and R₅, taken together with the nitrogen atom, form a N-pyrrolidinyl, piperidino or morpholino radical;

$R_2$ is $C_1$-$C_8$ alkyl or $C_3$-$C_4$ alkenyl;

$R_3$ is (a) furyl, thienyl or pyridyl, the furyl, thienyl and pyridyl grous being unsubstituted or substituted by a methyl group; or (b) the group

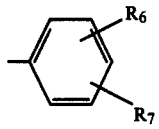

wherein each of $R_6$ and $R_7$ is independently selected from the group consisting of (a') hydrogen; (b') halogen; and (c') the group —(O)$_{n1}$—$R_8$, wherein $n_1$ is zero or 1 and $R_8$ is $C_3$-$C_4$ alkenyl or $C_1$-$C_6$ alkyl, the alkenyl and the alkyl groups being unsubstituted or substituted by one or more $C_1$-$C_2$ alkoxy or hydroxy groups, and a pharmaceutically acceptable salt thereof.

2. A compound of formula

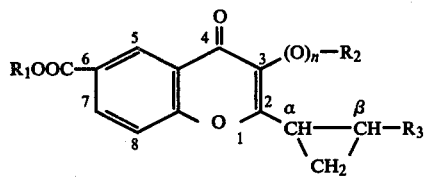

wherein $R_1$ is (a'') hydrogen; (b'') $C_1$-$C_6$ alkyl unsubstituted or substituted by a

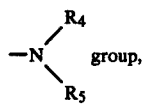

wherein each of $R_4$ and $R_5$, which are the same or different, is $C_1$-$C_4$ alkyl; (c'') 2-(N-pyrrolidinyl)-ethyl; (d'') pivaloyloxymethyl;

n is zero or 1;

$R_2$ is $C_1$-$C_4$ alkyl or $C_3$ alkenyl;

$R_3$ is (a''') phenyl unsubstituted or substituted by $C_1$-$C_4$ alkyl or $C_1$-$C_4$ alkoxy; or (b''') 2-furyl, 2-thienyl, 2-pyridyl, the furyl, the thienyl and the pyridyl groups being unsubstituted or substituted by a methyl group, and the pharmaceutically acceptable salts thereof.

3. A compound selected from the group consisting of:

trans 6-carboxy-3-propyl-2-(2-phenyl-cyclopropyl)-chromone;

trans 6-carboxy-3-allyl-2-(2-phenyl-cyclopropyl)-chromone;

trans 6-carboxy-3-ethoxy-2-(2-phenyl-cyclopropyl)-chromone;

trans 6-carboxy-3-butoxy-2-(2-phenyl-cyclopropyl)-chromone;

trans 6-carboxy-3-allyl-2-[2-(2'-methyl-phenyl)-cyclopropyl]-chromone;

trans 6-carboxy-3-ethoxy-2-[2-(2'-methyl-phenyl)-cyclopropyl]-chromone;

trans 6-carboxy-3-propyl-2-[2-(3'-methyl-phenyl)-cyclopropyl]-chromone;

trans 6-carboxy-3-allyl-2-[2-(3'-methyl-phenyl)-cyclopropyl]-chromone;

trans 6-carboxy-2-propyl-2-[2-(3'-methoxy-phenyl)-cyclopropyl]-chromone;

trans 6-carboxy-3-propyl-2-[2-(2'-methoxy-phenyl)-cyclopropyl]-chromone;

trans 6-carboxy-3-propyl-2-[2-(2'-pyridyl)-cyclopropyl]-chromone;

trans 6-carboxy-3-propyl-2-[2-(5'-methyl-2'-furyl)-cyclopropyl]-chromone;

trans 6-carboxy-3-ethoxy-2-[2-(5'-methyl-2'-furyl)-cyclopropyl]-chromone;

trans 6-carboxy-3-ethyl-2-[2-(2'-methyl-phenyl)-cyclopropyl]-chromone;

trans 6-carboxy-3-propyl-2-[2-(5'-methyl-2'-thienyl)-cyclopropyl]-chromone;

trans 6-carboxy-3-ethoxy-2-[2-(5'-methyl-2'-thienyl)-cyclopropyl]-chromone;

trans 6-carboxy-3-propyl-2-[2-(2'-methyl-phenyl)-cyclopropyl]-chromone 2-diethylaminoethyl ester;

trans 6-carboxy-3-propyl-2-[2-(5'-methyl-2'-furyl)-cyclopropyl]-chromone 2-diethylaminoethyl ester;

trans 6-carboxy-3-propyl-2-[2-(5'-methyl-2'-thienyl)-cyclopropyl]-chromone 2-diethylaminoethyl ester, as well as the pharmaceutically acceptable salts and the $C_1$-$C_6$ alkyl esters thereof.

4. A salt of a compound of claim 3, wherein the salt is the sodium salt.

5. A salt of a compound of claim 3, wherein the salt is the hydrochloride of a basic ester thereof.

6. A compound according to claim 5, wherein the basic ester is the 2-diethylaminoethanol or the 2-dimethylaminoethanol ester.

7. A $C_1$-$C_6$ alkyl ester of a compound of claim 3, wherein the $C_1$-$C_6$ alkyl group is methyl, ethyl, isopropyl, t-butyl or hexyl.

8. A pharmaceutical composition comprising a compound according to claim 1 and a pharmaceutically acceptable carrier and/or diluent.

9. Trans-6-carboxy-3-propyl-2-[2-(2'-methyl-phenyl)-cyclopropyl]-chromone, as well as the pharmaceutically acceptable salts and the $C_1$-$C_6$ alkyl esters thereof.

10. Method of claim 9, wherein said compound is administered orally or parentarally at a daily dosage of about 0.5 to about 15 mg/kg.

11. Method of claim 9, wherein said compound is administered by inhalation at a daily dosage of about 0.5 to about 100 mg.

12. Method of claim 9, wherein said compound is administered topically in a cream containing about 0.5 to about 5 mg of said compound per 100 mg of cream.

* * * * *

UNITED STATES PATENT AND TRADEMARK OFFICE
CERTIFICATE OF CORRECTION

PATENT NO. : 4,160,028
DATED : July 3, 1979
INVENTOR(S) : GIANFEDERICO DORIA ET AL It is certified that error appears in the above—identified patent and that said Letters Patent are hereby corrected as shown below:

Column 22, line 51, change "9" to -- 13 --.
Column 22, line 54, change "9" to -- 13 --.
Column 22, line 57, change "9" to -- 13 --.

Column 22, line 60, insert the following claim:

-- 13. A method of treating allergies in a host in need of such treatment, said method comprising administering to said host a therapeutically effective amount of a compound of claim 1. --

Signed and Sealed this

Twenty-seventh Day of November 1979

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,160,028

DATED : July 3, 1979

INVENTOR(S) : DORIA et al

It is certified that error appears in the above-identified patent and that said Letters Patent is hereby corrected as shown below:

Front page of the patent, Item [73]
delete "Carlo Erba S.p.A." and replace by --Farmitalia Carlo Erba S.p.A.--

Signed and Sealed this

Ninth Day of September 1986

[SEAL]

Attest:

DONALD J. QUIGG

Attesting Officer

Commissioner of Patents and Trademarks